(12) United States Patent
Lintell

(10) Patent No.: US 7,495,546 B2
(45) Date of Patent: Feb. 24, 2009

(54) DISPLAY SYSTEM

(75) Inventor: Daniel Thomas De Sausmarez Lintell, Ware (GB)

(73) Assignee: Glaxo Group Limited, Greenford, Middlesex (GB)

( * ) Notice: Subject to any disclaimer, the term of this patent is extended or adjusted under 35 U.S.C. 154(b) by 125 days.

(21) Appl. No.: 10/556,874

(22) PCT Filed: May 18, 2004

(86) PCT No.: PCT/EP2004/005489

§ 371 (c)(1), (2), (4) Date: Nov. 15, 2005

(87) PCT Pub. No.: WO2004/102375

PCT Pub. Date: Nov. 25, 2004

(65) Prior Publication Data

US 2007/0052544 A1    Mar. 8, 2007

(30) Foreign Application Priority Data

May 19, 2003  (GB)  .................. 0311461.8

(51) Int. Cl.
   *G08B 1/00*    (2006.01)

(52) U.S. Cl. .............. 340/309.7; 340/309.4; 340/309.8; 222/23; 128/200.14; 128/200.23

(58) Field of Classification Search .............. 340/309.7, 340/309.4, 309.8; 222/23; 128/200.14, 200.23
   See application file for complete search history.

(56) References Cited

U.S. PATENT DOCUMENTS

| | | |
|---|---|---|
| 4,223,801 A | 9/1980 | Carlson |
| 4,419,016 A | 12/1983 | Zoltan |
| 4,588,303 A | 5/1986 | Wirtschafter et al. |
| 5,363,842 A | 11/1994 | Mishelevich et al. |
| 5,392,952 A | 2/1995 | Bowden |
| 5,408,443 A | 4/1995 | Weinberger |
| 5,412,372 A | 5/1995 | Parkhurst et al. |
| 5,505,195 A | 4/1996 | Wolf et al. |
| 5,583,832 A | 12/1996 | DePonty |
| 5,642,731 A | 7/1997 | Kehr |
| 5,666,492 A | 9/1997 | Rhodes et al. |
| 5,809,997 A | 9/1998 | Wolf |
| 5,823,178 A | 10/1998 | Lloyd et al. |

(Continued)

FOREIGN PATENT DOCUMENTS

CA    2321230    9/1999

(Continued)

*Primary Examiner*—Tai T Nguyen
(74) *Attorney, Agent, or Firm*—James P. Riek

(57) ABSTRACT

A display system for use in displaying data in respect of usage of a device, the display system including: a detection system capable of detecting events that are indicative of usage of the device; and a display arranged to display data, the display system being arranged to invoke a selected display mode on the display, and being adapted, in response to detection of a given said event, to invoke a selected display mode, the display mode being selectable by the display system from a set of a plurality of different display modes in dependence on an elapsed time between a previous said event and said given event, each of the different display modes identifying a different stage of elapsed time.

16 Claims, 11 Drawing Sheets

U.S. PATENT DOCUMENTS

| | | | |
|---|---|---|---|
| 5,921,920 | A | 7/1999 | Marshall et al. |
| 6,012,450 | A | 1/2000 | Rubsamen |
| 6,014,969 | A | 1/2000 | Lloyd et al. |
| 6,018,289 | A | 1/2000 | Sekura et al. |
| 6,032,155 | A | 2/2000 | de la Huerga |
| 6,102,855 | A | 8/2000 | Kehr et al. |
| 6,148,815 | A | 11/2000 | Wolf |
| 6,198,383 | B1 | 3/2001 | Sekura et al. |
| 6,202,642 | B1 | 3/2001 | McKinnon et al. |
| 6,252,494 | B1 | 6/2001 | Howell |
| 6,304,797 | B1 | 10/2001 | Shusterman |
| 6,335,907 | B1 | 1/2002 | Momich et al. |
| 6,390,088 | B1 | 5/2002 | Nohl et al. |
| 6,435,175 | B1 | 8/2002 | Stenzler |
| 6,529,446 | B1 | 3/2003 | de la Huerga |
| 6,752,145 | B1 | 6/2004 | Bonney et al. |
| 6,958,691 | B1 | 10/2005 | Anderson et al. |
| 6,990,975 | B1 | 1/2006 | Jones et al. |
| 2001/0028308 | A1 | 10/2001 | de la Huerga |
| 2002/0070227 | A1 | 6/2002 | Ferruccio |
| 2002/0104848 | A1 | 8/2002 | Burrows et al. |
| 2002/0133061 | A1 | 9/2002 | Manetta |
| 2003/0192534 | A1* | 10/2003 | Klump et al. .......... 128/200.23 |
| 2005/0005934 | A1 | 1/2005 | Harvey |
| 2005/0081846 | A1* | 4/2005 | Barney ................. 128/200.23 |
| 2005/0161467 | A1* | 7/2005 | Jones ......................... 222/23 |

FOREIGN PATENT DOCUMENTS

| | | |
|---|---|---|
| EP | 0857456 | 8/1998 |
| EP | 0933092 | 8/1999 |
| EP | 1161933 | 12/2001 |
| GB | 2375758 A | 11/2002 |
| JP | 1993-5-184646 A | 7/1993 |
| JP | 5184646 | 7/1993 |
| JP | 8110735 | 4/1996 |
| JP | 2511016 | 6/1996 |
| JP | 2001-343475 A | 12/2001 |
| JP | 2001343475 | 12/2001 |
| WO | WO 99/38556 | 8/1999 |
| WO | 9943284 | 9/1999 |
| WO | WO 00/21598 | 4/2000 |
| WO | WO 01/41845 | 6/2001 |
| WO | WO 01/50434 | 7/2001 |
| WO | 01/66061 A1 | 9/2001 |
| WO | WO 01/93801 | 12/2001 |
| WO | 02/05039 A1 | 1/2002 |
| WO | 02/24257 A1 | 3/2002 |
| WO | 02/30497 A1 | 4/2002 |
| WO | 02/32487 A1 | 4/2002 |
| WO | 0239366 | 5/2002 |
| WO | 02/058767 A1 | 8/2002 |
| WO | 02/058771 A1 | 8/2002 |
| WO | 02078593 | 10/2002 |
| WO | WO 02/078593 | 10/2002 |
| WO | 02/100470 A1 | 12/2002 |
| WO | 03035508 | 5/2003 |

* cited by examiner

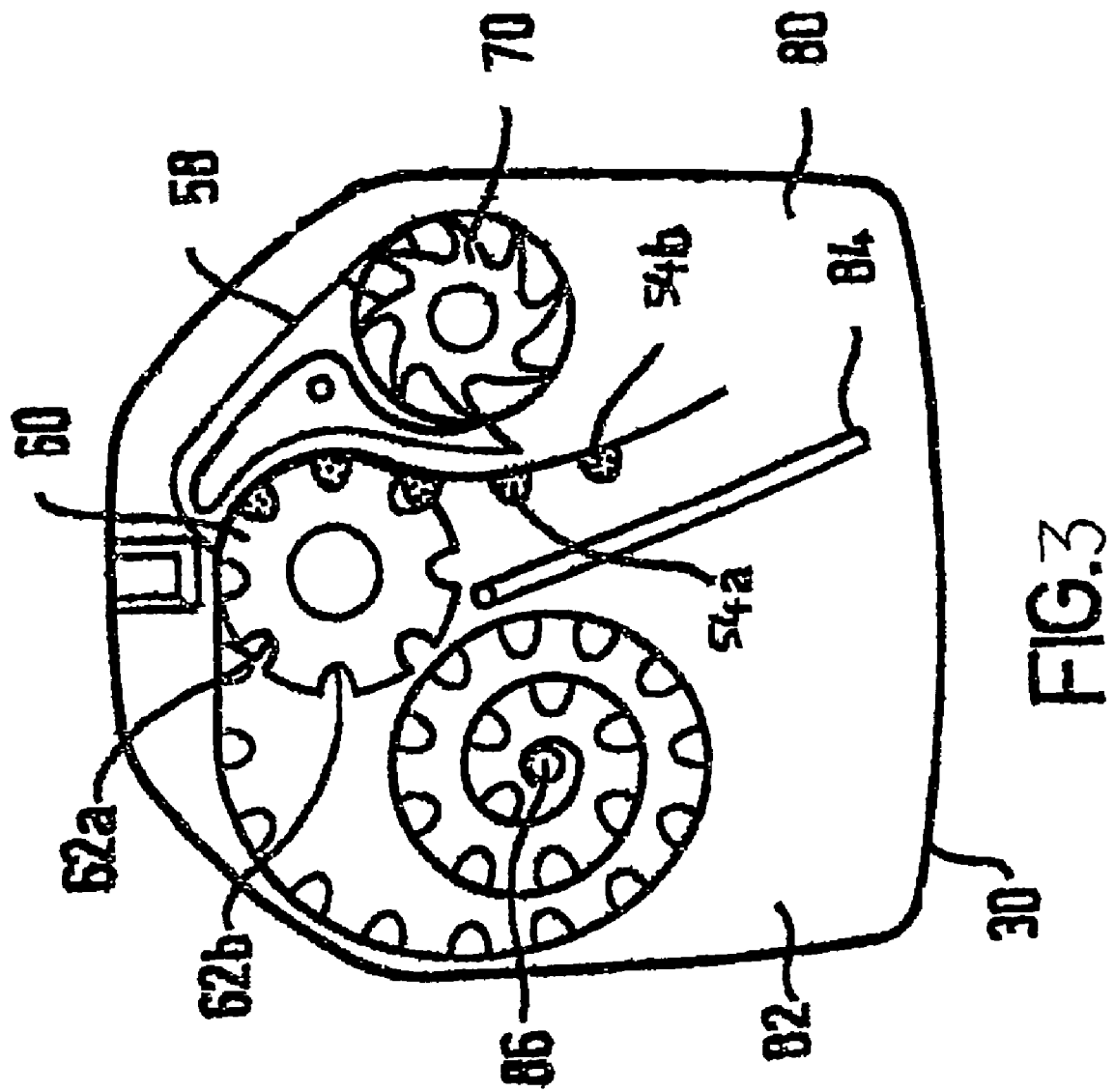

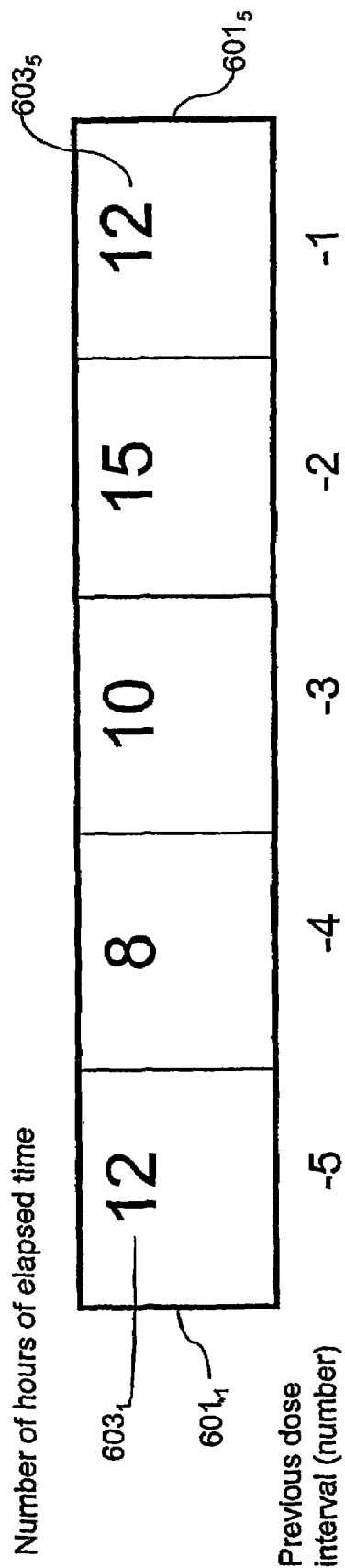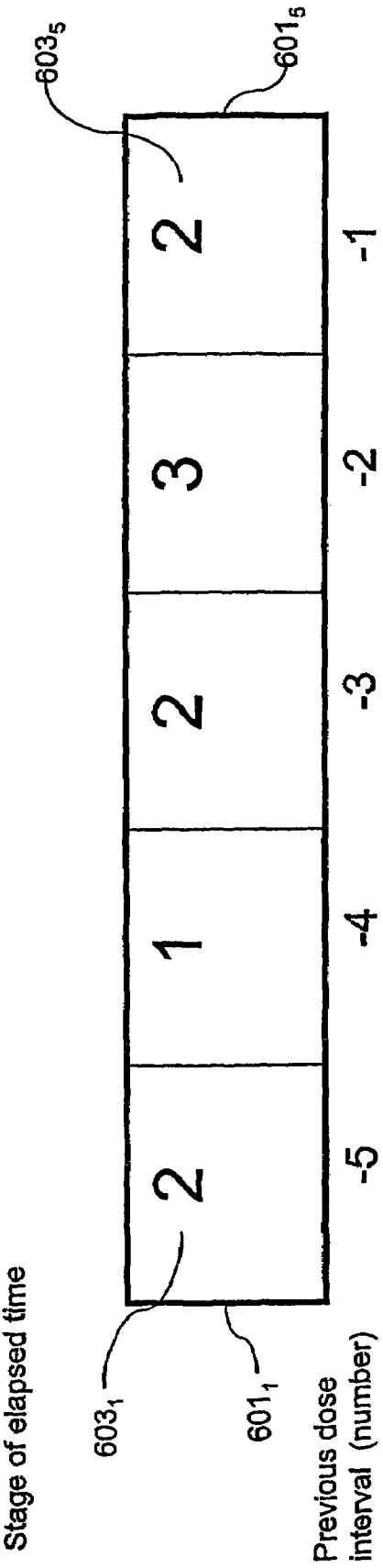
FIG. 9a
FIG. 9b

DISPLAY SYSTEM

CROSS-REFERENCE TO RELATED APPLICATIONS

This application is filed pursuant to 35 U.S.C. § 371 as a United States National Phase Application of International Application No. PCT/EP2004/005489 filed May 18, 2004 which claims priority from GB 0311461.8 filed May 19, 2003.

FIELD OF THE INVENTION

The present invention relates to a display system for use in displaying data in respect of usage of a device. The invention particularly, but not exclusively, relates to a display system for use with a device arranged to dispense a product.

BACKGROUND OF THE INVENTION

For patients, compliance with medical treatment regimens appears to be extremely difficult; according to the United States Food and Drug Administration (FDA), between 30 and 50 percent of patients fail to use medicines as prescribed (as described by Dixie Farley in "FDA Proposes Program to Give Patients Better Medication Information", published in FDA Consumer magazine (November 1995)). The main problems with compliance include taking an incorrect dose, failing to take doses at the set time, missing doses and ceasing treatment prematurely, any one of which can, in the best case, prolong the recovery period, and in the worst case, result in a failure to treat the patient's condition at all.

A solution to this problem, which is advocated by the FDA, is for patients to keep a record of the names, doses, regimens of current medications; to discuss their treatment with a pharmacist or doctor regularly; and to follow the instructions given by these physicians. However, this approach relies on patients proactively monitoring and recording their medicament behaviour, and thus relies on the very aspect of human nature that, thus far, has made patient compliance so poor.

Several companies have been active in the development of medicament dispensers that record and store data indicative of medicament events, the data being subsequently downloaded to a centralised database for analysis by a physician. For example, U.S. patent application US2002/0104848 describes a system including a dispenser having a sensor adapted to sense opening of the dispenser cover (this being deemed indicative of dispensing of medicament) and a control unit adapted to store a time at which such an opening event has been detected. Data indicative of this event, which essentially provides a dispensing history, are stored on the dispenser and accessed by a base station, which communicates the data to a patient database for review by a physician. However, it is difficult for the patient to directly receive compliance information, since he has to rely on feedback from the physician. This means that the patient can only receive compliance information by consulting with his physician, which, to be successful, again relies on the patient making and keeping appointments.

In alternative systems, the dispensing device is arranged to display the times at which medicament have been dispensed on the device itself. For example, U.S. Pat. No. 5,642,731 describes a medicament dispenser having a sensor adapted to sense opening of the doors of the dispenser, a control unit adapted to store a time at which such an opening event has been sensed, and an electronic display having a menu from which the user can select one of a plurality of display options. One of these options corresponds to a review of the actual times that an opening event has been sensed (this being deemed indicative of dispensing of medicament) within a prescribed period (e.g. a number of hours or a number of days). The patent goes on to describe graphically displaying percentage compliance over time, together with symptom severity over time, recognising that patients are more likely to persevere with a treatment regimen if they can "see" their symptoms improving. However, displaying such information requires input from the user in relation to their symptoms, thus again relying on patients taking a proactive role in their treatment.

It would be desirable to provide a device that is of greater convenience to the user.

SUMMARY OF THE INVENTION

According to a first aspect of the present invention there is provided a display system for use in displaying data in respect of usage of a device, the display system including:
 a detection system capable of detecting events that are indicative of usage of the device; and
 a display arranged to display data,
 wherein the display system is arranged to invoke a selected display mode on the display, and being adapted, in response to detection of a given said event, to invoke a selected display mode, the display mode being selectable by the display system from a set of a plurality of different display modes in dependence on an elapsed time between a previous said event and said given event, each of the different display modes identifying a different stage of elapsed time.

Embodiments of the invention are suitable for use with devices that are arranged to dispense a product, where events relating to usage of such a device include, for example, opening of the device, removal of the device from a holder (where applicable), or dispensing of the product contained therein. The detection system can thus comprise one or more sensors arranged to detect these operations.

One such dispensing device is a medicament dispenser, and an event indicative of usage of a medicament dispenser can be an event relating to the dispensing of medicament, such as movement of a refill within the medicament dispenser. Thus the detection system can be provided by a sensor arranged to detect such refill movement. Such a display system allows the user to review the stage of elapsed time, relative to a previously taken dose, at which the given dose was taken. The user can then associate the various stages with the regimen (e.g. early, due, late) and embodiments of the invention immediately inform the user of whether the given dose was taken early, at the due time or late with respect to a previously taken dose. Thus in comparison to the prior art systems discussed above, the display system provides compliance information with a reduced amount of input from the user.

Preferably the display includes a plurality of regions, each region corresponding to a different stage of elapsed time in relation to said previous event and a selectable display mode distinguishes whichever region corresponds to the stage of elapsed time in which said previous event occurred from at least one of the other regions. In one arrangement the display system is arranged to display an indicium indicative of said previous event in said region, whilst in another arrangement said region comprises portions arranged to illuminate at predetermined intervals. Alternatively the display includes a common display region and the selected display mode displays an indicium therein, wherein each of the selectable display modes displays a different indicium in said common display region, each indicium being selectable from a plurality of indicia and representing a different stage of elapsed time in relation to said previous event. In either configuration, a selectable display mode can include displaying an identifier representative of an integral number of hours corresponding to the stage of elapsed time since the previous event occurred.

Conveniently the display system is arranged to invoke a plurality of display modes, each corresponding to a different given event, and the elapsed time upon which the selection of each of the plurality of display modes is based is dependent on an event previous to said different given event and said different given event. Since selection of one display mode is dependent on the time between two events, three or more previous events are required in order to display two or more display modes. Preferably each display mode relates to successively occurring pairs of events, and the display graphically provides information relating to the amount of elapsed time between such successively occurring pair of events. Each event defines both the end of a previous pair of events and the start of a next pair of events, which means that the elapsed times between successively occurring pairs of events, and thus display modes, are directly comparable. Since invoking a display mode involves displaying indicia on the display, the user is immediately provided with information regarding the consistency or irregularity with which successive events have occurred. In the context of medicament dispensers, this is particularly useful, since it immediately shows the user both his compliance with a regimen (that is to say correlation between a time that the user should have taken a dose and the time that he actually took a dose) and the regularity with which he takes a series of doses.

According to a second aspect of the present invention there is provided a display system for use in displaying data in respect of events that are indicative of usage of a device, the display system being arranged to invoke a selected display mode on a display, the display mode being selectable from a plurality of different display modes, wherein the display system is adapted to invoke a selected display mode in response to detecting a said event, the display mode being selected by the display system in dependence on when said event is detected, wherein the display includes a plurality of regions, and the selected display mode distinguishes one of said plurality of regions from at least one other of said plurality of regions.

Preferably the display system is arranged to invoke a plurality of display modes, each corresponding to a different given event. In this second aspect, selection of display mode is either dependent on time relative to a previous event or is based on absolute time. When selection is based on absolute time, the interval between successive events that occur once daily may be identical to a cycle of the 24 hour clock (i.e. 24 hours). This means that each of a plurality of display modes selected in accordance with the actual time at which an event occurred can be directly compared with another such event in order to identify the regularity or otherwise with which successive events occur.

Further features and advantages of the invention will become apparent from the following description of preferred embodiments of the invention, given by way of example only, which is made with reference to the accompanying drawings.

BRIEF DESCRIPTION OF THE DRAWINGS

FIG. 3 shows a schematic view of an internal mechanism of a cassette in accordance with an embodiment of the present invention;

FIGS. 5a, 5b, 5c, 6, 7, 9a, 9b and 10 illustrate alternative display configurations showing various display modes selected in dependence on an elapsed time between a previous event and said given event;

DETAILED DESCRIPTION OF THE INVENTION

Figure 1:
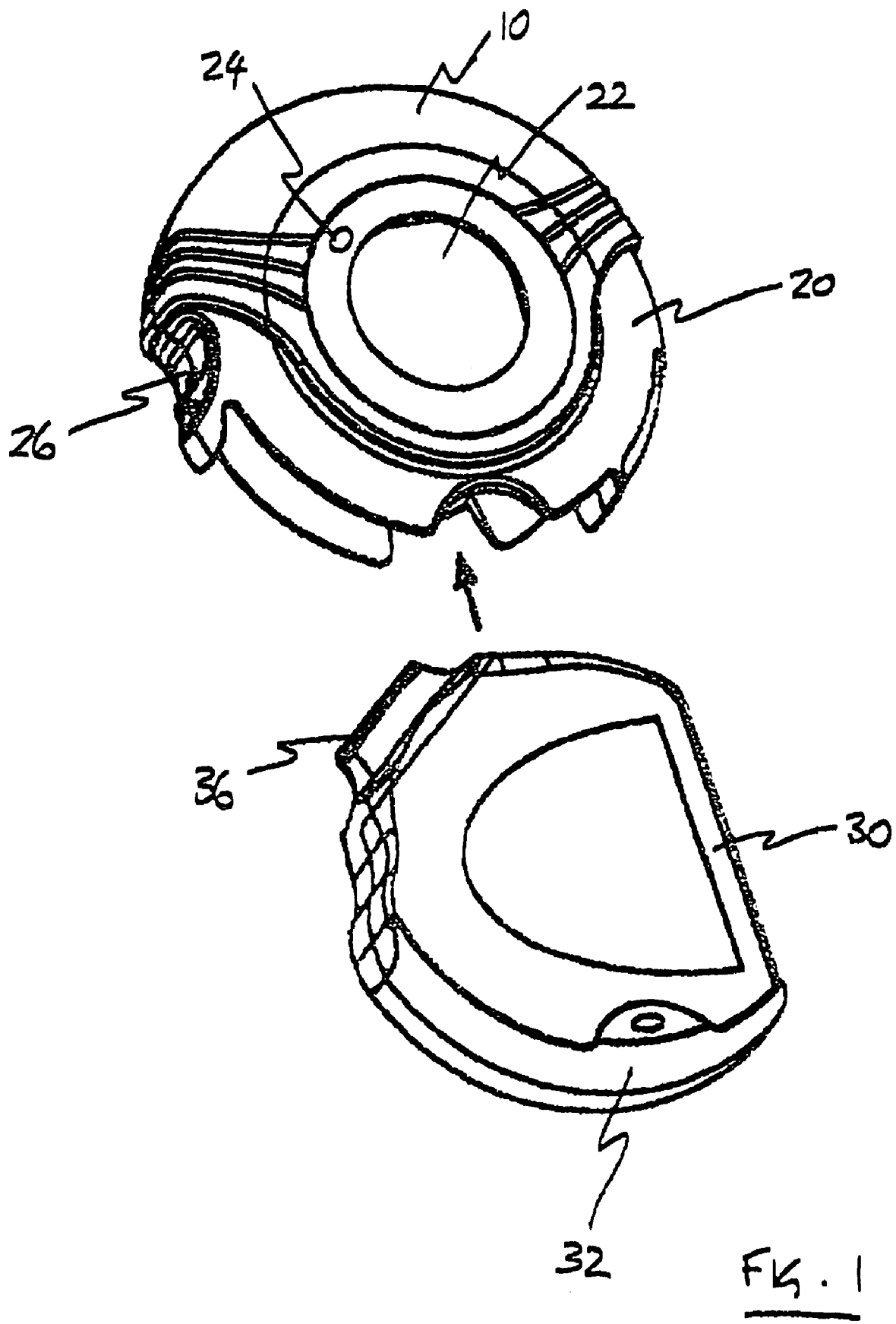
FIG. 1 shows a perspective view of a medicament dispenser within which an embodiment of the invention operates, with the cassette removed from the holder and body.

Embodiments of the display system according to the invention are exemplified within a medicament dispenser such as that shown in FIG. 1, in the form of a base unit comprising an outer cover 10 and a holder 20, and a refill cassette 30. In this example the medicament dispenser is a dry powder inhaler adapted for oral inhalation. The holder 20, which includes an electronic display 22, is shaped to fit inside cover 10 and is fixed to the body via a bearing (not shown) about which it rotates coaxially. Stops (not shown) protrude from the holder 20 and prevent the holder 20 from rotating more than about 180° relative to the cover 10. The stops also provide two defined positions of the holder 20 within the cover 10. An outer part of the holder is shaped in the form of a concave recess 26 to provide a thumb or finger grip for the user of the device. The holder 20 forms a recess into which the refill cassette 30 latches.

The refill cassette 30 comprises a shell containing the medicament carrier and a mechanism for opening the carrier for the medicament to be accessed. The refill cassette 30 has a rear portion 32 which is exposed by a cut-away part of the holder 20 when the rest of the cassette 30 is contained within the holder 20 so as to allow the cassette to be manually gripped for removal from the holder 20.

The refill cassette 30 also has a mouthpiece 36 from which a user inhales medicament dispensed from the cassette 30.

Figure 2A:
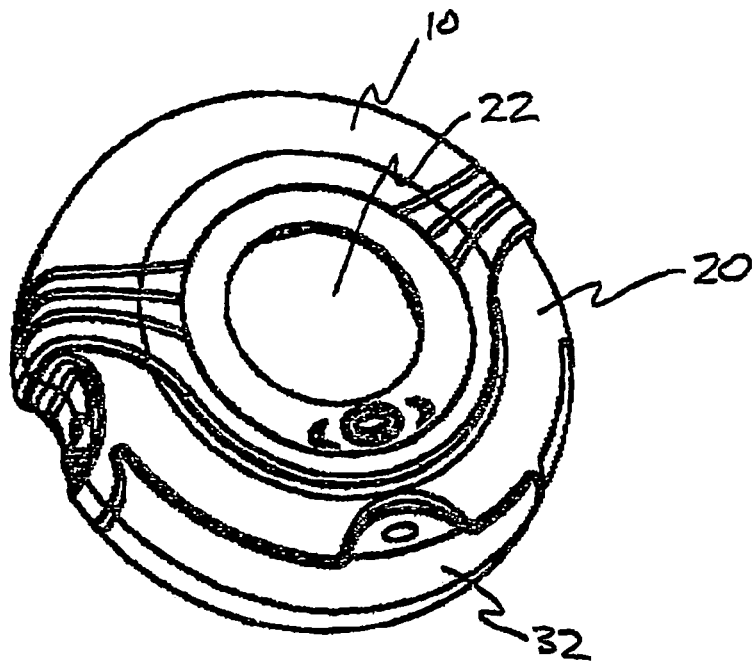
FIG. 2a shows a plan view of the medicament dispenser of FIG. 1 with the cassette in the non-dispensing position.

FIG. 2a shows the medicament dispenser with the cassette 30 in place in the holder 20 and with cover 10 in a non-dispensing position in which the rear end 32 of the cassette is exposed. The cassette 30 is fixed in place by a spring-biased catch (not shown). When the cassette 30 is in the position shown, relative to the holder 20, the cover 10 covers the mouthpiece (not shown). The cover 10 also protects the thumbtab 28 of an indexing lever (not shown) and this prevents accidental indexing of the medicament carrier when the medicament dispenser is not in use.

Figure 2B:
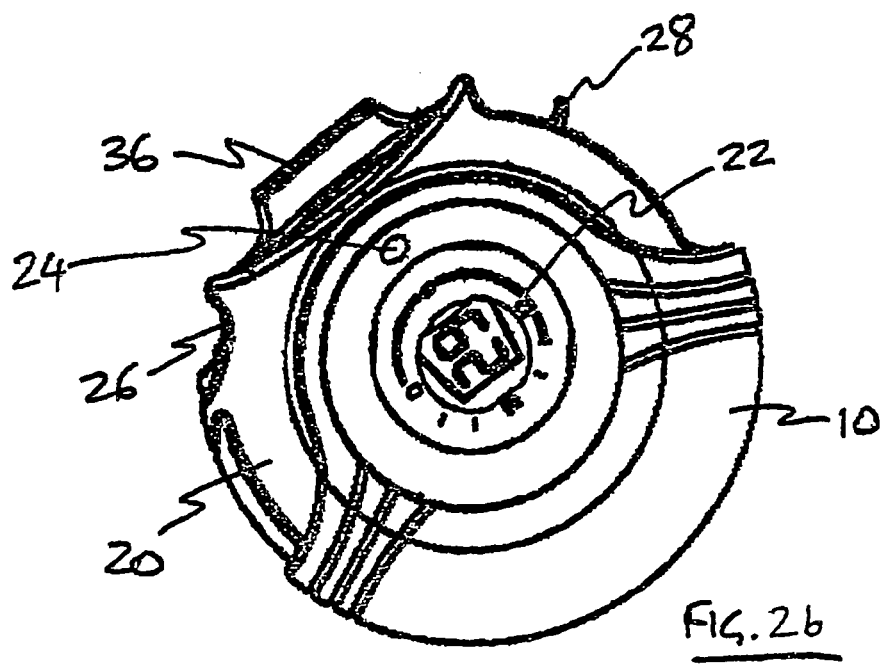
FIG. 2b shows a plan view of the medicament dispenser of FIGS. 1 and 2a with the cassette in the dispensing position.

FIG. 2b shows the medicament dispenser of FIGS. 1 and 2a with the cassette 30 in place in the holder 20 in a dispensing position. The holder 20 has been rotated relative to the cover 10 so that a stop on the holder 20 abuts the cover 10. It can be seen that the holder 20 has a further cut away portion to expose the mouthpiece 36.

FIG. 3 schematically shows an internal mechanism of a refill cassette 30 containing a medicament carrier, in the situation where the majority of the pockets are still filled with discrete doses of medicament in the form of dry powder. The internal mechanism comprises an index wheel 60 and a lid-winding wheel 70 for winding the used portion of the lid sheet 58. The index wheel 60 has a plurality of recesses 62a, 62b extending parallel with the axis of the wheel. The recesses 62a, 62b are spaced at a pitch which is equal to the distance between the centre lines of adjacent pockets 54a, 54b.

The cassette 30 also includes an area 80 for the medicament carrier to be coiled up prior to use of the doses contained inside it and an area 82 where the used base of the medicament carrier is collected. Area 82 contains base winding wheel 86 on which the used portion of the base sheet is wound, and a spindle mechanism (not shown) is arranged to unidirectionally rotate the index wheel 60 and the lid-winding wheel 70 in unison with base winding wheel 86.

In operation, the user moves the holder relative to the body to move the cassette into the dispensing position and then presses on the finger tab of the lever to cause it to move. This leads to rotation of the index wheel 60 which results in rotation on both the base winding wheel 86 and the lid winding wheel 70, thus peeling the base sheet and lid sheet apart over a distance sufficient to expose a previously unopened pocket opposite the end of the powder outlet. The patient can then inhale the powdered medicament through the mouthpiece FIG. 2b shows the thumbtab 28 of the indexing lever in a reset position, ready for actuation. Actuation of the thumbtab 28 indexes the medicament carrier within the refill cassette 30, thereby exposing a dose of medicament ready for inhalation through the mouthpiece 36. The display 22 shown in FIG. 2b includes a graphical representation of a set of indicia representative of time elapsed and a set of dose count indicia, to be described in further detail below.

Figure 4:
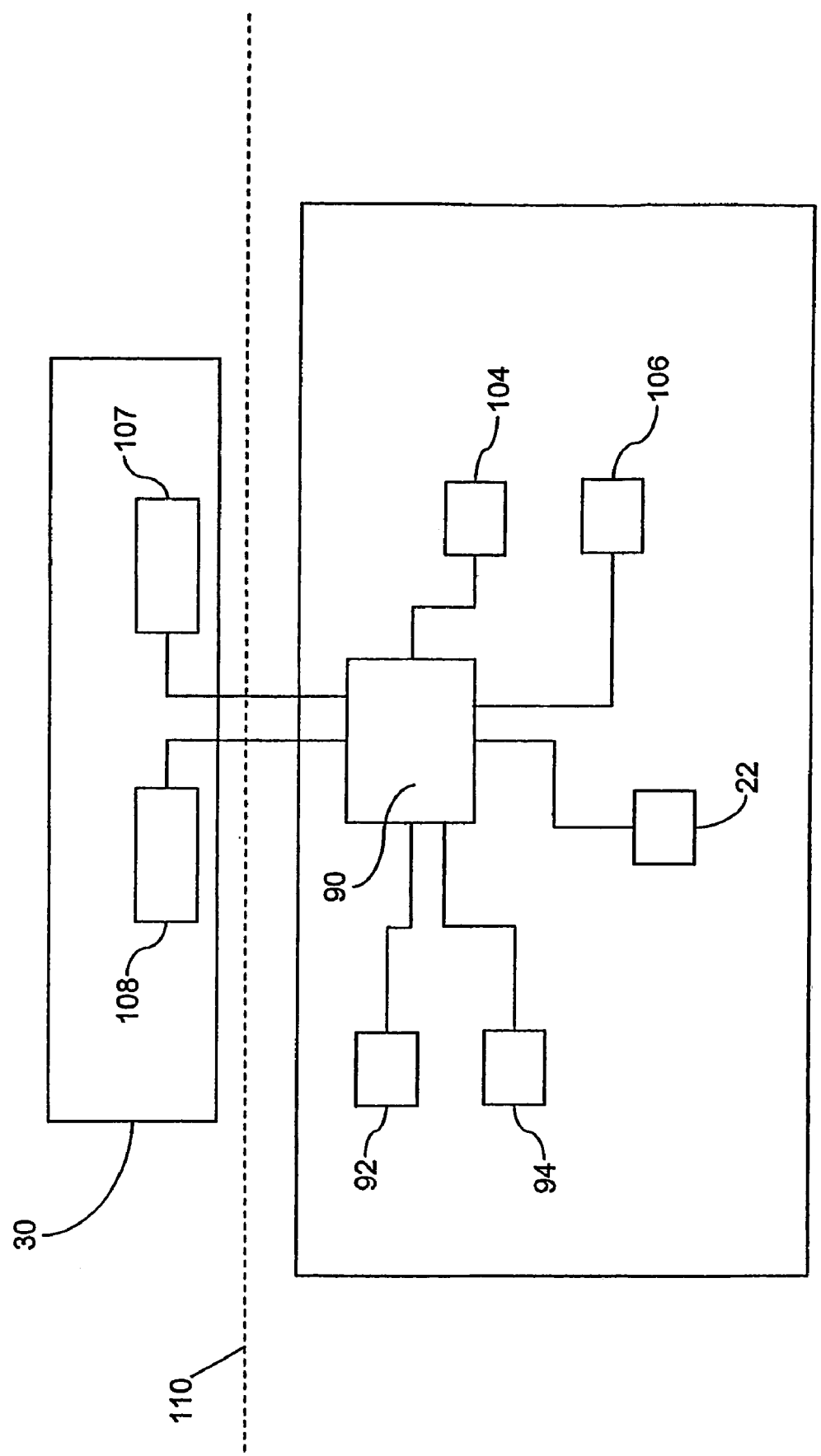
FIG. 4 is a schematic block diagram of an electronic subsystem of the medicament dispenser.

FIG. 4 is a schematic block diagram of the electronic subsystem of the medicament dispenser. The holder 20 includes an in-built control unit 90, for example in the form of a microprocessor chip, including an internal clock. Various sensors are electrically connected to the control unit 90, including a battery voltage sensor 92, which monitors, against a threshold, voltage of a battery providing electrical power to the medicament dispenser, also housed in the holder 20. In some arrangements, the control unit 90 can include a cover open sensor 94, which senses movement of the cover relative to the holder from the non-dispensing position, in which the cover covers the mouthpiece of the dispenser, to an open position in which medicament may be dispensed.

Embodiments of the invention are concerned with aspects of display systems, and in particular, with aspects that can be usefully employed by medicament systems to provide compliance data. In the context of compliance, embodiments are concerned with improving a user's appreciation for how well or badly he is complying with a preferred regimen, that is to say the correlation between the time that a user actually dispenses medicament and the time that the medicament should be dispensed.

In embodiments of the invention, a display mode is selected in response to detection of a given event relating to usage of a device, and the selection is dependent on the time at which the given event occurred. In one embodiment, display mode selection is dependent on the time between occurrence of a previous event and occurrence of the given event, whilst in another embodiment the selection is dependent on the actual time that the given event occurs. Thus one embodiment is based on relative time, thus providing the user with information that enables them to ascertain the stage, in relation to the previous event, at which the given event occurred, whilst the other embodiment is based on absolute time.

In the context of medicament dispensers, an event comprises taking a dose of medicament, so that the display mode provides the user with information that enables them to ascertain the stage, in relation to the time of the previously taken dose, to which the given event corresponds. In one embodiment, the stages include "early" or "due" or "late", which tells the user that the event (i.e. time at which the user took a dose) was either "early", "due" or "late" in relation to the previously taken dose (previous event).

Various embodiments of the invention, integrated with a medicament dispenser, will now be described in more detail.

Referring back to FIG. 4, the control unit 90 includes means for detecting that a dose has been taken; in a first arrangement the means comprises dose sensor 107, which is part of the refill cassette 30. The dose sensor 107 is in data communication with the control unit 90 via a data communication interface 110, which uses a transceiver in the control unit 90 and a transceiver in the sensor 107. When the index wheel 60 is rotated, the dose sensor 107 senses said rotation, and transmits a signal to the control unit 90 indicating that a dose is about to be taken (the assumption being that a dose will subsequently be taken).

Various conditions of the medicament dispenser may be sensed by means of the electronic subsystem illustrated in FIG. 4, including the stage of elapsed time since a previous dose was dispensed. After a dose has been dispensed and/or inhaled, the control unit 90 begins a time elapsed function, which monitors time that has elapsed since the previous dose was sensed to have been taken. Once a next dose is detected to have been taken, the elapsed time function stops, and the amount of elapsed time between the previously taken dose and the most recently taken dose is used by the control unit 90 to select a display mode. The control unit 90 is operatively connected to the display 22, and selection of an appropriate display mode causes one or more identifiers to be displayed on the display 22. Thus in this embodiment the display system is provided by the control unit 90.

Each of FIGS. 5a, 5b, 5c, 6, 7, 9a, 9b, 10 and 11 shows alternative embodiments of screen configuration for the display 22, whereby the display modes may be indicated to the user. In at least one embodiment each of the display modes causes indicia to be presented on a segmented LCD display. Note that, below, the description of elements of each of the screen configurations is to be understood to apply to the same indicia displayed in each of the different screen configurations where the same numerical references, incremented by multiples of 100, are used. Although the exact form of the indicia are different, their functions and the control thereof by the control unit 90 are similar and therefore should be understood that the description in relation to indicia in one configuration applies equally to similarly referenced indicia in different configurations.

A first embodiment will now be described, with reference to FIG. 5a; in this and the following embodiments, the previous event, from which the elapsed time is measured, will be referred to as a first event, and the event following the previous event, whose occurrence defines the stage of elapsed time, will be referred to as a second event. Thus referring firstly to FIG. 5a, in a first embodiment the display 22 comprises three regions 501a, 501b, 501c, which for example each separately indicates a different stage of elapsed time between the time at which the first event occurred and the time at which the second event occurred. Preferably the regions 501a, 501b, 501c are provided by static indicia.

The first region 501a corresponds to an "early" stage, and indicates that the stage of elapsed time between occurrences of the first and second events is early with respect to the regimen for this medicament; the second region 501b corresponds to a "due" stage, and indicates that that the stage of elapsed time between occurrences of the first and second events is in accordance with the regimen for this medicament; and the third region 501c corresponds to a "late" stage, thus indicating that the stage of elapsed time between occurrences of the first and second events is late with respect to the regimen for this medicament. Clearly it is not necessary for the regions 501a, 501b, 501c to be defined in this precise manner, and in other arrangements a display may include more than 3 regions. However, preferably each of the regions has a particular meaning in relation to the regimen for the medicament. In this, and later figures, these regions 501a, 501b, 501c are assigned different patterns (dots, stripes, bricks respectively) to aid identification of a particular region. Preferably each region 501a, 501b, 501c would have a different colour (or, if the display 22 is black and white, a different shade of grey), and the user would be informed which colour (or shade) relates to the different stages. Alternatively or additionally each region 501a, 501b, 501c could have text therein, e.g. respectively "early", "On time!" and "late".

In this example a display mode is selected from a possible 3 display modes (only one—the third—is shown), a first with indicium 503 in the "early" region 501a, a second with indicium 503 in the "due" region 501b and a third (FIG. 5c) with indicium 503 in the "late" region 501c. In this embodiment, the display mode distinguishes whichever region corresponds to the stage of elapsed time from the other regions by means of activatable indicium 503. As an alternative, the region corresponding to the stage of elapsed time between the first and second events (here region 501c) could flash, or the border of the region could be emboldened, thereby increasing the prominence of the corresponding region 501c compared to the other regions 501a, 501b.

Figure 5:
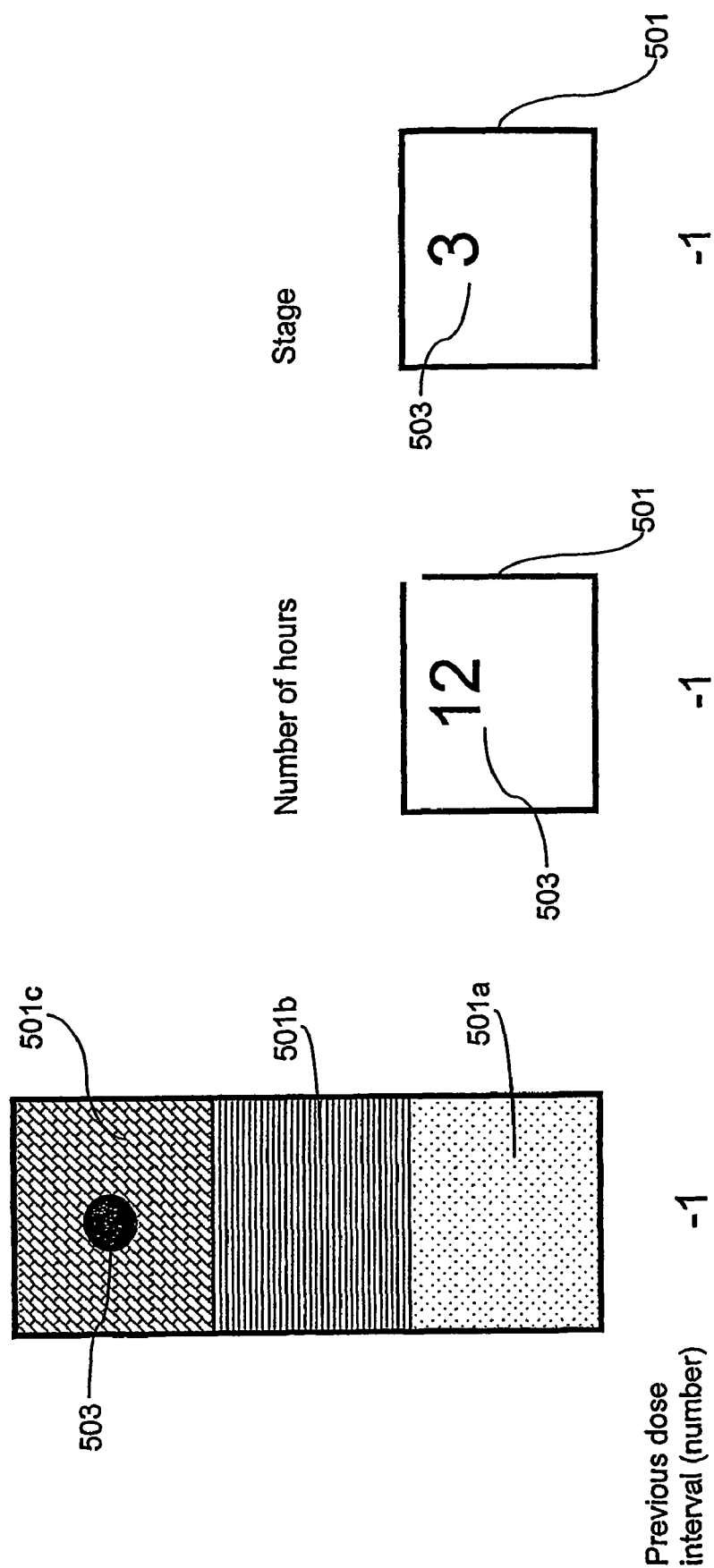

Turning to FIGS. 5b and 5c, the display could alternatively have one activatable region 501, in which indicium 503 indicative of the stage is presented. In one arrangement (FIG. 5b), the selected display mode indicates the number of hours of elapsed time between the occurrence of the first event and the occurrence of the second event, whilst in another arrangement (FIG. 5c) the selected display mode indicates the stage of elapsed time, which is essentially equivalent to identifying one of the plurality of regions shown in FIG. 5a. As an alternative to indicating the stage number (1 . . . 3), each stage could be associated with a symbol so that the indicium 503 includes the appropriate symbol. In the arrangement shown in FIG. 5b, therefore, there could be 24 display modes, and in the arrangement shown in FIG. 5c, there could be 2 or more display modes.

Thus in this embodiment the actual time that a dose was taken is not presented to the patient; instead the patient is presented with information indicative of the time between doses. Since, at a minimum, the patient can be expected to know the time period between doses, this embodiment advantageously enables the patient to review his progress in relation to the drug regimen.

Figure 6:
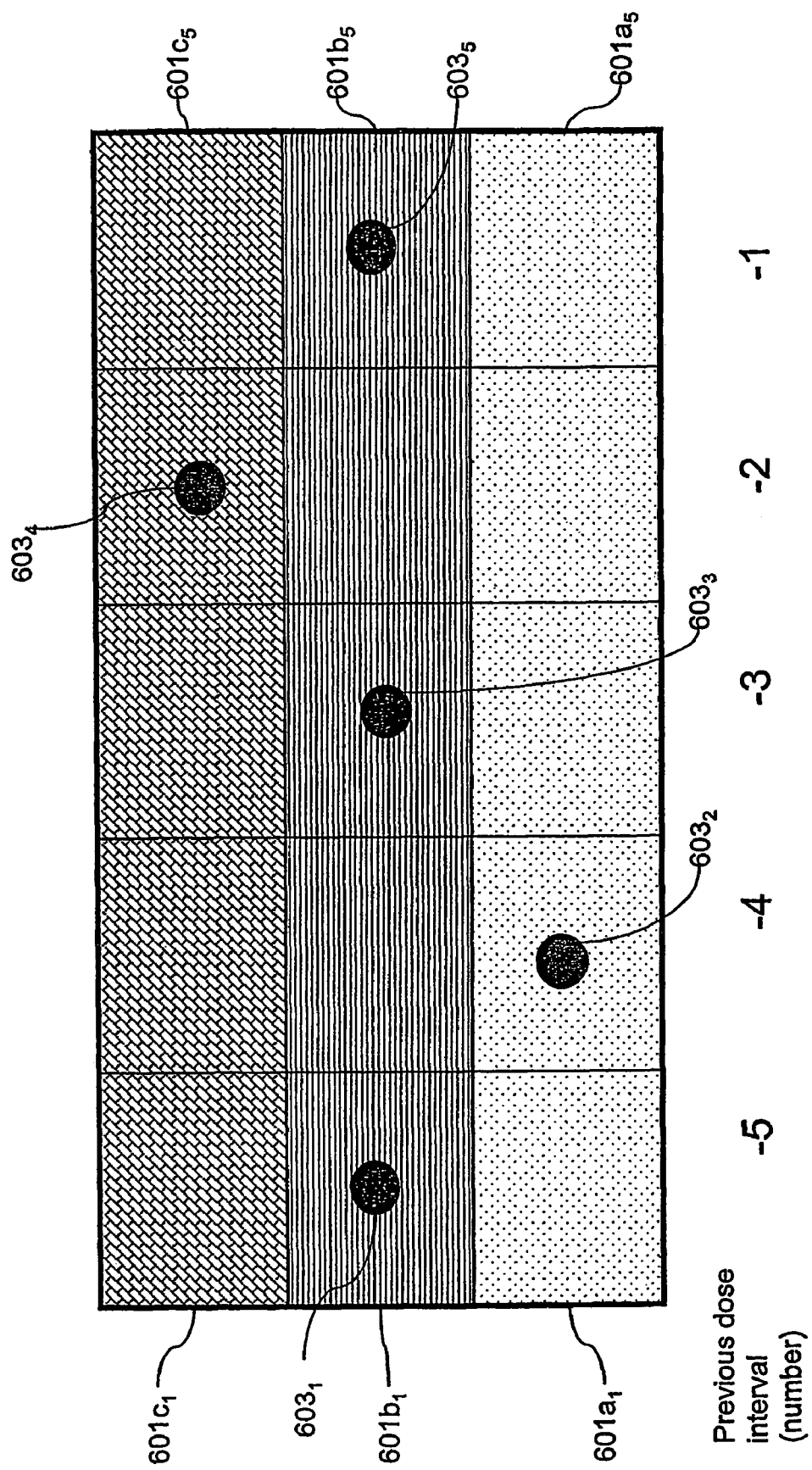

FIG. 6 shows a second embodiment of the invention, which corresponds to the arrangement shown in FIG. 5a, wherein the display 22 comprises a plurality of regions. In this embodiment, the display 22 is configured to show data relating to a plurality of previous events, specifically six previous events. For each successive pair of events a display mode is selected, in dependence on the elapsed time between the two events in the pair. In this example there are five pairs of events: a first pair between first and second events, which corresponds to a first display mode; a second pair between second and third events, which corresponds to a second display mode; a third pair between third and fourth events, which corresponds to a third display mode; a fourth pair between fourth and fifth events, which corresponds to a fourth display mode; and a fifth pair between fifth and sixth events, which corresponds to a fifth display mode. In the Figure only regions $601a_1$, $601b_1$, $601c_1$, which correspond to the time between the first and second events, and regions $601a_5$, $601b_5$, $601c_5$, which correspond to the time between the fifth and sixth events, are referenced (for clarity).

Each display mode is selectable from the three display modes as described above (so that the indicium $603_i$ is located in one of the three regions $601a_i$, $601b_i$, $601c_i$). FIG. 6 thus shows five selected display modes, each having been selected in dependence on the elapsed time between the two events in the pair, and including indicium $603_1$, $603_2$, $603_3$, $603_4$, $603_5$ indicating the stage of elapsed time between the two events forming the pair.

The display 22 therefore provides a graphical representation of compliance with the regimen both for individual doses and for a succession of doses. It thus provides a means of tracking the variation in times that doses have been taken, and enables the patient to immediately see the regularity (or lateness) with which medication has been taken.

Figure 7:
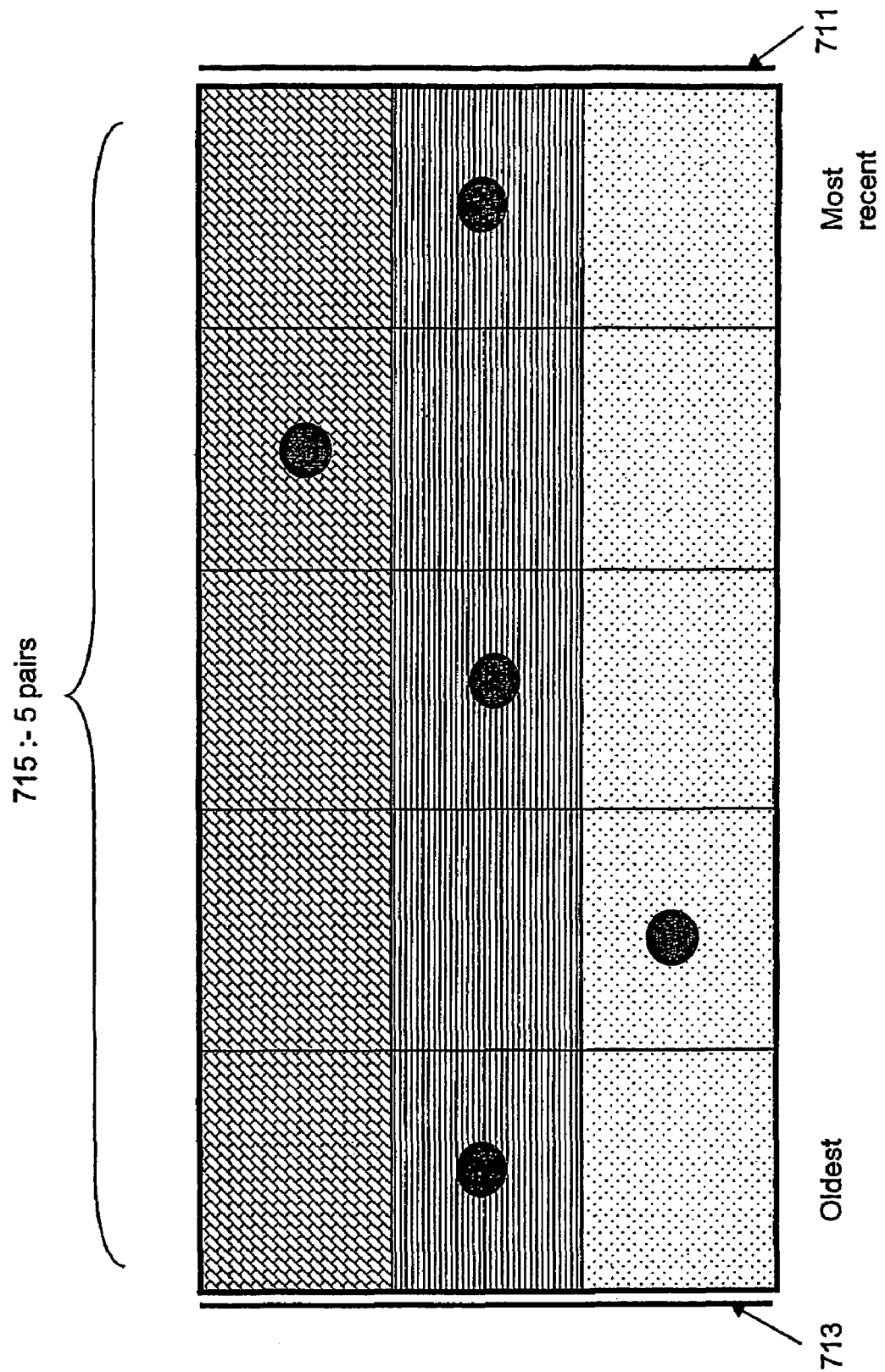

Typically the display 22 is limited by space constraints, which means that only a limited number of pairs of previous events (dispensing history) can be displayed. Referring to FIG. 7, the display 22 has a first end 711 a second end 713, a specified length 715 corresponding to a number of pairs of events, or selected display modes, and is adapted to include wrap-around functionality. Assuming data to have been received in respect of the specified number of pairs of events, a display mode selected in relation to a subsequently detected event is displayed on the first end 711, thereby displacing data displayed at the second end 713. In this arrangement the oldest display mode currently on the screen is deleted from the second end of the screen.

In the foregoing embodiments the regions correspond to periods of time having different lengths, and the lengths of these periods are regimen-dependent. For example, in the case of a once daily regimen, the "early" stage (corresponding to region 501a, $601a_i$) could extend between 0 and 20 hours, while the "due" stage (corresponding to region 501b, $601b_i$) could correspond to 20-28 hours and the "late" stage (corresponding to region 501c, $601c_i$) to any number of hours in excess of 28 hours; in the case of a twice daily regimen, the "early" stage could extend between 0 and 9 hours, while the "due" stage could correspond to 9-15 hours and the "late" stage to any number of hours in excess of 15 hours; in the case of a thrice daily regimen, the "early" stage could extend between 0 and 6 hours, while the "due" stage could correspond to 6-10 hours and the "late" stage to any number of hours in excess of 10 hours; etc. Clearly the control unit 90 controlling the display 22 either has to receive data identifying the regimen to which the medicament corresponds, which it can use to set the extents of the regions 501a, 501b, 501c, or the medicament dispenser will be tailored to a specific regime, so that the extents of the regions 501a, 501b, 501c will be hard-wired therein.

Assuming the control unit 90 to be configured to read regimen information from the refill cassette 30, such regimen information can be provided on a memory chip 108 (shown in FIG. 4), which is in data communication with the control unit 90 via data communication interface 110. The control unit 90 can then use a timing regimen, which may be preset in the control unit 90 or read from the memory chip 108, to determine the periods of time corresponding to the regions. This process will now be described in more detail with reference to FIG. 8, for the example of the arrangement shown in FIG. 5a. At step 801, the control unit 90 reads the regimen information stored on the refill cassette 30, and identifies, at step 803, the extents of the regions 501a, 501b, 501c. Assuming the regimen information to indicate that the medicament should be taken twice daily, step 803 involves the control unit 90 processing an algorithm adapted to calculate the boundaries for a twice daily medicament; in the event that the boundary information is stored on the refill cassette, step 803 merely involves reading the boundary data from the refill. The control unit 90 then waits (step 804) for a signal from the dose sensor 107, indicating that a dose has been taken.

Once such a signal has been received, and if this is a first time that the base unit has been used, the control unit 90 resets its internal clock at step 805 and waits (step 804) for the next signal. However, if this is a second or subsequent signal, the control unit 90 reads (step 806) the current timer value associated with the internal clock, resets the internal clock at step 807 and, using the timer value, selects (step 809) a display mode from the 3 possible display modes using the timer value read at step 806. In the event that the information identified at step 803 indicates that the "early" stage corresponds to 0-8 hours, the "due" stage corresponds to 8-15 hours and the "late" stage corresponds to any time exceeding 15 hours, and assuming the timer data read at step 806 to be 10 hours, the control unit 90 will select (step 809) the display mode in which the indicium 503 is present in the "due" region 501b. The control unit 90 then invokes (step 811) the display mode selected at step 809 and reverts to checking for a next signal (step 804).

It should be noted that the internal clock of the control unit 90 can be arranged to track the elapsed time independently of the presence or otherwise of a refill 30. This means that the monitoring of elapsed time between events is unaffected by the replacement of a refill 30, and the control unit 90 can continue to record the interval between the last dose of one refill cassette and the first dose of a next refill cassette.

As described above, the display 22 has a first side 711 and a second side 713, and display modes relating to the most recent event are invoked in a display area closest to the first side 711. If the display mode selected at step 809 is the first display mode, step 811 involves displaying indicia relating to the selected display mode in the display area closest to this first side 711. However, if the display mode selected at step 809 is the second or subsequently invoked display mode, step 811 additionally involves displacing indicia currently displayed on the display 22 towards the second end 713 of the display 22. As described above, the display 22 is of a limited size, and can only show data relating to a specified number of previous doses. Assuming that the display 22 includes regions corresponding to six previous events, meaning that at most five display modes can be invoked at the same time, the control unit 90 checks (step 821) whether the signal currently being processed relates to the sixth or a subsequent event before invoking the display mode selected at step 809. If this is the case, at step 823 the control unit 90 replaces the indicia displayed in the regions located closest to the second end 713 of the display 22 by displacing the indicia located in the other regions towards the second end 713 (as part of step 811).

As described with reference to FIGS. 5b and 5c, as an alternative to the display comprising a plurality of regions, one of which can be distinguished from at least one other region to indicate the stage of elapsed time between the occurrence of the first event and the occurrence of the second event, the display can comprise a single region having indicia therein. In this alternative arrangement, a selected display mode results in indicia(um) being invoked in the region. The indicia either indicate the number of hours of elapsed time, or the stage of elapsed time, between the occurrence of the first event and the occurrence of the second event. FIGS. 9a and 9b show data relating to a plurality of previous events, specifically six previous events (thus five previous dose intervals and selection of five display modes), and are equivalent to FIG. 6. An advantage of displaying the number of hours since a previous dose is that the variation in take times over a series of doses is more apparent than when the stage number is displayed (or, for that matter, when the display comprises 2 or more regions, each corresponding to a stage), since each stage corresponds to several hours and there is no way of telling where, within that stage, the dose was taken.

Figure 8:
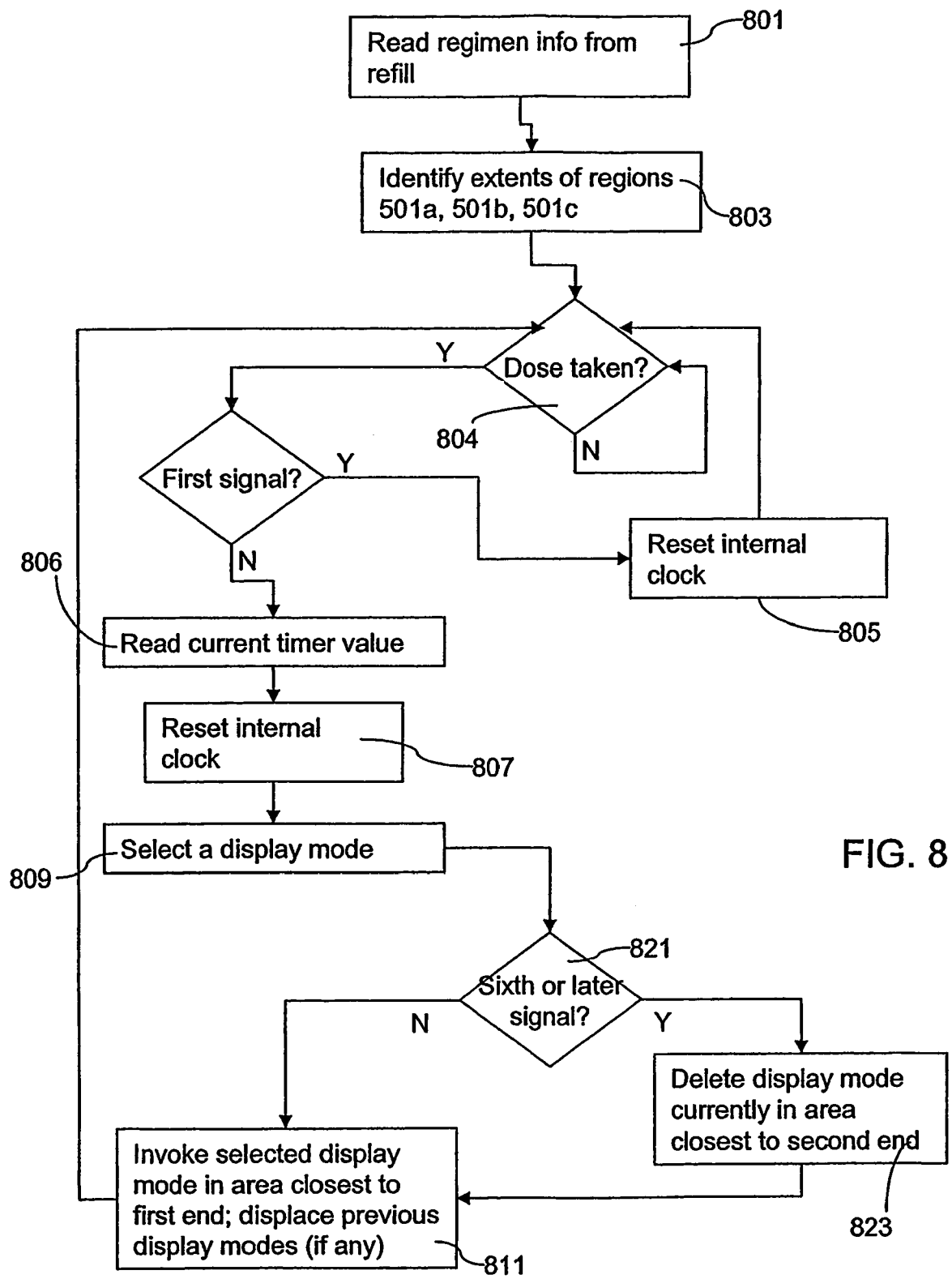
FIG. 8 is a flow diagram showing steps carried out by the electronic subsystem shown in FIG. 4 when selecting and invoking display modes in accordance with an embodiment of the invention.
Figure 10:
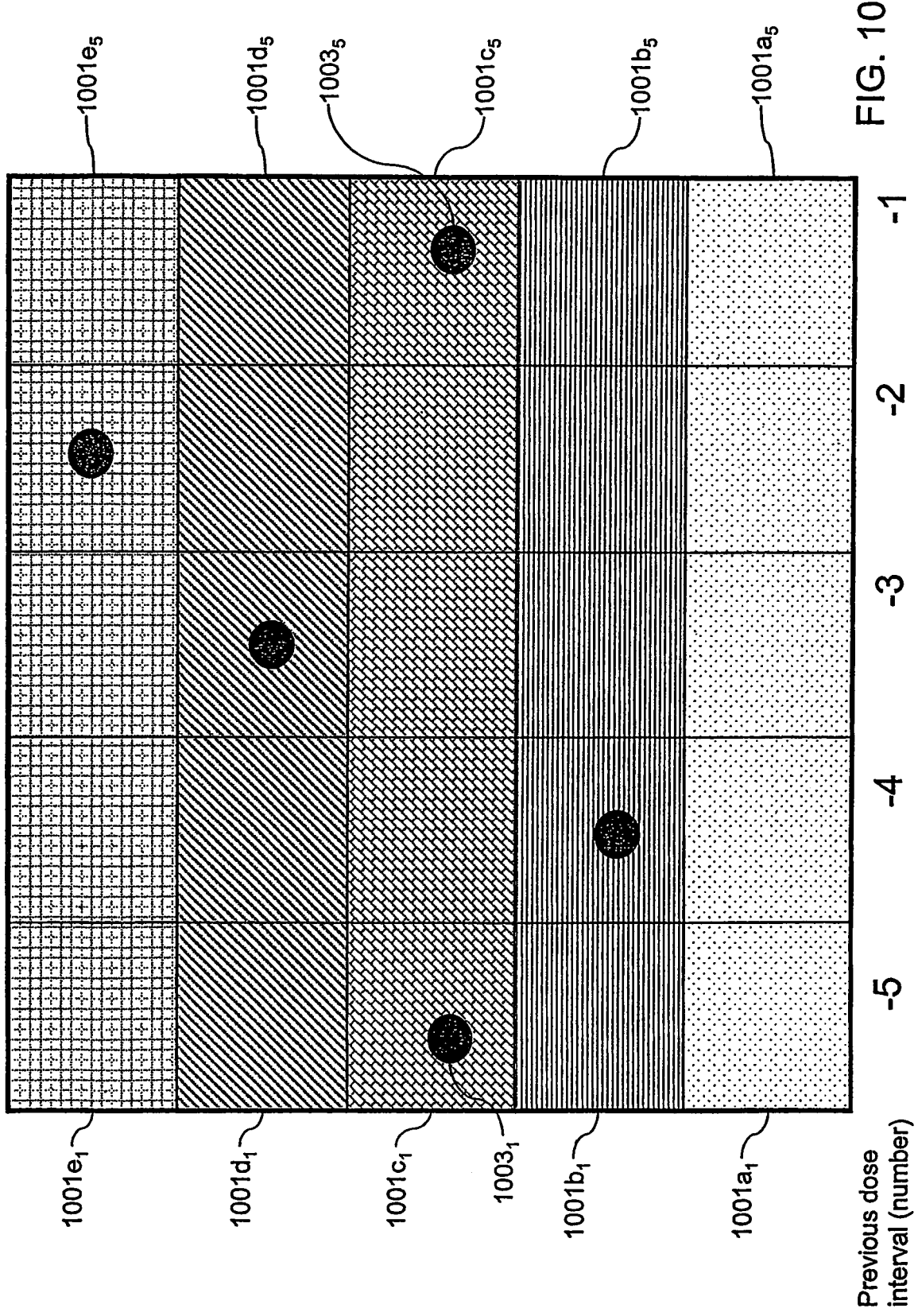

In the first and third arrangements described above (relating to FIGS. 5a and 5b and FIGS. 6 and 9b), regimen information is used to determine the extents of the regions on the display (i.e. stages of elapsed time "early", "due", "late" (1, 2, 3 respectively)). However, in an alternative embodiment the regions are arranged so as to be independent of regimen, and steps 801 and 803 described in FIG. 8 are redundant. Referring to FIG. 10, in one embodiment each display comprises five regions 1001a, 1001b, 1001c, 1001d, 1001e, and the extents thereof are distributed as follows: a first region 1001a corresponds to an elapsed time of between 0 and 5 hours (thus relating to an "early" stage of elapsed time in respect of all of the regimens). A second region 1001b corresponds to an elapsed time of between 5 and 10 hours (which relates to an "early" stage of elapsed time in respect of the once and twice daily regimes and a "dose due" stage of elapsed time in respect of the thrice and four times a day regimens (since for the thrice a day regimen a dose is due at 8 hours, and for the four times a day regimen a dose is due at 6 hours)). A third region 1001c corresponds to an elapsed time of between 10 and 19 hours (which relates to a "dose due" stage of elapsed time in respect of the twice daily regime, an "early" stage of elapsed time in respect of the once daily regimen and a "late" stage of elapsed time in respect of the thrice daily and four times a day regimens). A fourth region 1001d corresponds to an elapsed time of between 19 and 25 hours (this relates to a "dose due" stage of elapsed time in respect of the once daily regimen and a "late" stage of elapsed time in respect of the twice, thrice daily and four times a day regimens). A fifth region 1001e corresponds to an elapsed time in excess of 25 hours (this relates to a "late" stage of elapsed time in respect of all of the regimens). Thus if a patient were on a four times daily regimen, his physician could indicate that the display modes should include the indicium 1003 in the second region 1001b, whilst if a patient were on a once daily regimen, the physician could indicate that the display modes should include the indicium 1003 in the fourth region 1001d.

This embodiment is advantageous from a manufacturing point of view, since the same dispenser can be used for four different regimens, and there is no need to include software and/or hardware required to set the extents of the regions 501a, 501b, 501c. A particularly valuable aspect of this embodiment is that it provides a means of tracking, with greater visibility, the variation in take times over a series of doses. With increasing numbers of regions, the amount of information about the degree of variation increases. If a patient wants to know how early or how late he was with a previous dose it may be preferable to have more, rather than less, regions. However, the number of regions will be limited by the size of the display 22, so that for larger displays each display may include five or more such regions, whilst for smaller displays each display may include three regions. Where the size of the display is extremely limited the single region arrangements (corresponding to FIGS. 5b and 5c) may be preferred; thus when indicium indicative of the stage number is displayed (corresponding to FIG. 5c), the indicium can vary between the number 1 and the number 5, or alternatively some symbol indicative of numbers 1-5.

Figure 11:
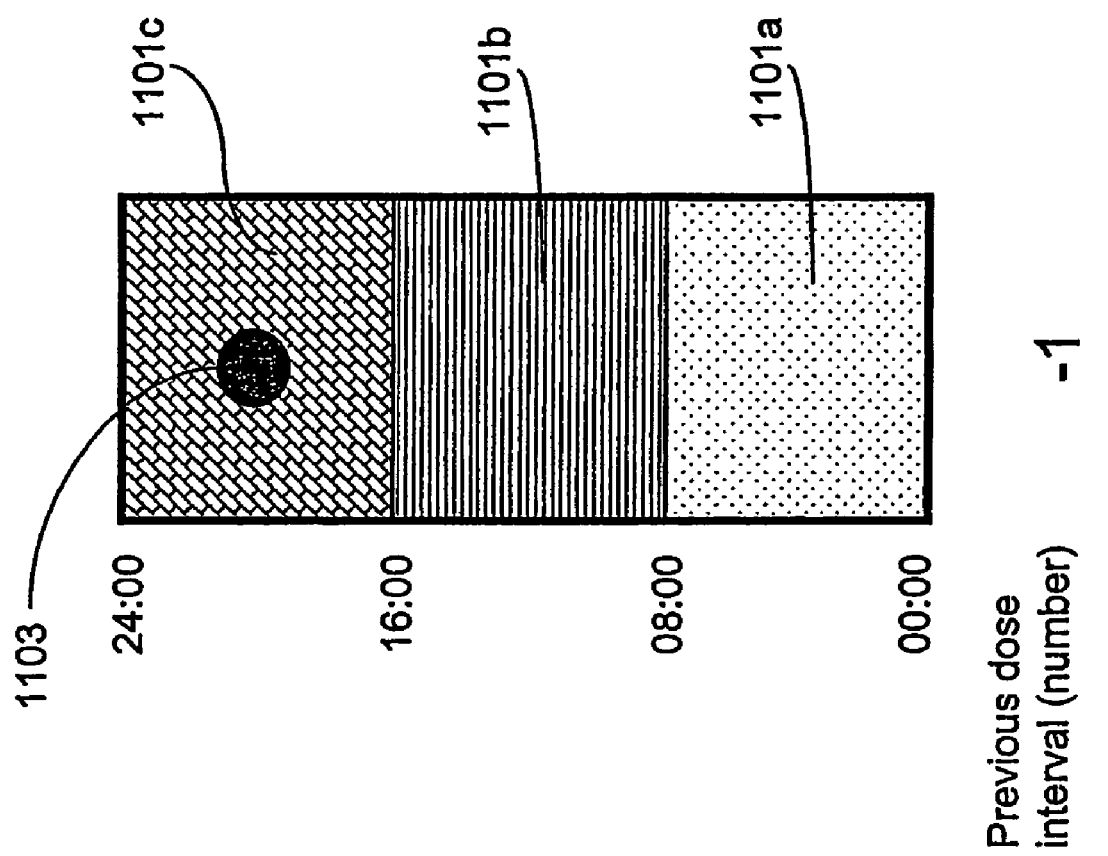
FIG. 11 illustrates a screen configuration showing a display mode selected in dependence on the actual time of the given event.

In the embodiments described above, selection of display mode is based on relative time, so that the regions on the display 22 correspond to periods of elapsed time between doses. However, in an alternative embodiment the regions on the display 22 could correspond to absolute times. Absolute time is itself relative, in that time is reset after 24 hours. The dosage interval on a once daily regimen medicament is thus identical to that of the 24 hour clock, meaning that, for the once daily regimen, display modes selected in accordance with absolute time are equivalent to selecting display modes in accordance with elapsed time between two successive doses. This means that in addition to ascertaining the time at which a dose has been taken, dose history can be tracked by inspecting the trend in display modes (as for the foregoing embodiments). Referring to FIG. 11, a first region 1101a could correspond to 00:00-08:00, and a second region 1101b could correspond to 08:00-16:00 hours and a third region 1101c could correspond to 16:00-24:00 hours. As for the embodiments described above, invoking a display mode involves inserting indicium 1103 into whichever of the regions corresponds to the time that an event was detected, the indicium 1103 being a marker, a symbol or any visual identifier that distinguishes the pertinent region from the other regions.

Whilst in the foregoing embodiments the events forming a pair of events are described as being successive events, they could either be sequential or non-sequential events.

In the foregoing embodiments an event relating to the dispensing of medicament is described as being detected by means of movement of the index wheel 60. However, the detection system can be arranged to detect other events that are indicative of usage of the dispenser. These events include opening the cover 10, changes in flow rate and changes in pressure through the mouthpiece 36, so that the detection system can include a cover-movement detector and/or a pressure measuring device arranged to measure static and dynamic pressure (e.g. with a piezo-electric crystal). Referring back to FIG. 4, the detection system can additionally or alternatively include a radiation emitter 104, which emits radiation into the mouthpiece, and an inhalation sensor 106, which detects the emitted radiation on the other side of the mouthpiece. When the user inhales, the medicament powder causes scattering of the radiation emitted by radiation emitter 104, thereby reducing the detected level of radiation at inhalation sensor 106, and indicating inhalation of a dose. In the case of the medicament dispenser being located in a holder until such time as medication is to be dispensed, removal of the dispenser could also be an event indicative of usage of the dispenser, in which case the detection system can comprise a light emitter and detector pair located in the holder, which cooperatively provide a signal indicative of the presence, or removal, of the dispenser from the holder.

Whilst in the foregoing description the embodiments have been described as forming a part of a medicament dispenser, the display system (embodied in the control unit 90) could also be used medicament contexts, since the display system essentially provides support for any events that involve usage of a device on a regular basis. For example, the display system could be used in conjunction with an electric toothbrush, where an action indicative of usage of a device comprises, e.g., removing the toothbrush from its holder.

In the above, the display 22 takes the form of a segmented LCD display. In a segmented LCD display, the display indicia are formed by means of individual liquid crystal elements which are preconfigured in the display screen, and which may be separately activated under the control of the control unit 90. An advantage of using a segmented display is increased clarity, along with reduced cost. The display may be monochrome or colour. Again, for increased clarity and reduced cost, a monochrome display is preferred. The display may take other forms, for example, comprise a screen such as an LED arrangement or a pixellated LCD display. The display may be embodied using analogue or digital technology.

Whilst the memory chip 108 is described as communicating with the control unit 90 via electrical contacts, the memory chip 108 may be in the form of a radio frequency (RFID) tag, and the data communications interface 110 may be a wireless data communications interface.

A medicament dispenser according to the invention is suitable for dispensing medicament, particularly for the treatment of respiratory disorders such as asthma and chronic obstructive pulmonary disease (COPD).

Appropriate medicaments may thus be selected from, for example, analgesics, e.g., codeine, dihydromorphine, ergotamine, fentanyl or morphine; anginal preparations, e.g., diltiazem; antiallergics, e.g., cromoglycate (e.g. s the sodium salt), ketotifen or nedocromil (e.g. as the sodium salt); anti-infectives e.g., cephalosporins, penicillins, streptomycin, sulphonamides, tetracyclines and pentamidine; antihistamines, e.g., methapyrilene; anti-inflammatories, e.g., beclomethasone (e.g. as the dipropionate ester), fluticasone (e.g. as the propionate ester), flunisolide, budesonide, rofleponide, mometasone e.g. as the furoate ester), ciclesonide, triamcinolone (e.g. as the acetonide) or 6α, 9α-difluoro-11β-hydroxy-16α-methyl-3-oxo-17α-propionyloxy-androsta-1, 4-diene-17β-carbothioic acid S-(2-oxo-tetrahydro-furan-3-yl) ester; antitussives, e.g., noscapine; bronchodilators, e.g., albuterol (e.g. as free base or sulphate), salmeterol (e.g. as xinafoate), ephedrine, adrenaline, fenoterol (e.g. as hydrobromide), formoterol (e.g. as fumarate), isoprenaline, metaproterenol, phenylephrine, phenylpropanolamine, pirbuterol (e.g. as acetate), reproterol (e.g. as hydrochloride), rimiterol, terbutaline (e.g. as sulphate), isoetharine, tulobuterol or 4-hydroxy-7-[2-[[2-[[3-(2-phenylethoxy)propyl]sulfonyl]ethyl] amino]ethyl-2(3H)-benzothiazolone; adenosine 2a agonists, e.g. 2R,3R,4S,5R)-2-[6-Amino-2-(1S)-hydroxymethyl-2-phenyl-ethylamino)-purin-9-yl]-5-(2ethyl-2H-tetrazol -5-yl)-tetrahydro-furan-3,4-diol (e.g. as maleate); $\alpha_4$ integrin inhibitors e.g. (2S)-3-[4-({[4-(aminocarbonyl)-1-piperidinyl]carbonyl}oxy) phenyl]-2-[((2S)-4-methyl-2-{[2-(2-methylphenoxy) acetyl]amino}pentanoyl) amino] propanoic acid (e.g. as free acid or potassium salt), diuretics, e.g., amiloride; anticholinergics, e.g., ipratropium (e.g. as bromide), tiotropium, atropine or oxitropium; hormones, e.g., cortisone, hydrocortisone or prednisolone; xanthines, e.g., aminophylline, choline theophyllinate, lysine theophyllinate or theophylline; therapeutic proteins and peptides, e.g., insulin or glucagon; vaccines, diagnostics, and gene therapies. It will be clear to a person skilled in the art that, where appropriate, the medicaments may be used in the form of salts, (e.g., as alkali metal or amine salts or as acid addition salts) or as esters (e.g., lower alkyl esters) or as solvates (e.g., hydrates) to optimise the activity and/or stability of the medicament.

Preferred medicaments are selected from albuterol, salbutamol, salmeterol, fluticasone propionate and beclomethasone dipropionate and salts or solvates thereof, e.g., the sulphate of albuterol and the xinafoate of salmeterol.

Medicaments can also be delivered in combinations. Preferred formulations containing combinations of active ingredients contain salbutamol (e.g., as the free base or the sulphate salt) or salmeterol (e.g., as the xinafoate salt) or formoterol (e.g. as the fiunarate salt) in combination with an antiinflammatory steroid such as a beclomethasone ester (e.g., the dipropionate) or a fluticasone ester (e.g., the propionate) or budesonide. A particularly preferred combination is a combination of fluticasone propionate and salmeterol, or a salt thereof (particularly the xinafoate salt). A further combination of particular interest is budesonide and formoterol (e.g. as the fumarate salt).

Generally, powdered medicament particles suitable for delivery to the bronchial or alveolar region of the lung have an aerodynamic diameter of less than 10 micrometers, preferably less than 6 micrometers. Other sized particles may be used if delivery to other portions of the respiratory tract is desired, such as the nasal cavity, mouth or throat. The medicament may be delivered as pure drug, but more appropriately, it is preferred that medicaments are delivered together with excipients (carriers) which are suitable for inhalation. Suitable excipients include organic excipients such as polysaccharides (i.e. starch, cellulose and the like), lactose, glucose, mannitol, amino acids, and maltodextrins, and inorganic excipients such as calcium carbonate or sodium chloride. Lactose is a preferred excipient.

Particles of the powdered medicament and/or excipient may be produced by conventional techniques, for example by micronisation, milling or sieving. Additionally, medicament and/or excipient powders may be engineered with particular densities, size ranges, or characteristics. Particles may comprise active agents, surfactants, wall forming materials, or other components considered desirable by those of ordinary skill.

The excipient may be included with the medicament via well known methods, such as by admixing, co-precipitating and the like. Blends of excipients and drugs are typically formulated to allow the precise metering and dispersion of the blend into doses. A standard blend, for example, contains 13000 micrograms lactose mixed with 50 micrograms drug, yielding an excipient to drug ratio of 260:1. Dosage blends with excipient to drug ratios of from 100:1 to 1:1 may be used. At very low ratios of excipient to drug, however, the drug dose reproducibility may become more variable.

It will be understood that the present disclosure is for the purpose of illustration only and the invention extends to modifications, variations and improvements thereto, and that any elements of the different embodiments may be combined to form further embodiments of the invention.

The application of which this description and claims form part may be used as a basis for priority in respect of any subsequent application. The claims of such subsequent application may be directed to any feature or combination of features described therein. They may take the form of product, method or use claims and may include, by way of example and without limitation, one or more of the appended claims.

The invention claimed is:

1. A display system for use in displaying data in respect of usage of a device, the display system including:
   a detection system to detect an event that is indicative of usage of the device; and
   a display arranged to display data;
   the display system being arranged to invoke a selected display mode on the display in response to detection of the said event, the display mode being selectable by the display system from a set of a plurality of different display modes in dependence on an elapsed time between detection of the said event and a previous detection of said event, each of the different display modes identifying a different stage of elapsed time between detection of the pair of said events,
   wherein the display system is arranged to invoke a plurality of said display modes, each corresponding to a respective one in a sequence of a plurality of detections of said event comprising at least first, second and third detections of said event, and the elapsed time upon which the selection of each of the plurality of display modes is based is dependent on the elapsed time between the corresponding detection of said event in the sequence and a previous detection of said event in said sequence.

2. A display system according to claim 1, wherein the display system is arranged to invoke on the display a plurality of regions for each display mode, for each display mode each region corresponding to a different stage of elapsed time between the corresponding detection of said event and said previous detection of said event, and the display system is arranged to distinguish whichever region in each display mode corresponds to the stage of elapsed time between the corresponding detection of said event and said previous detection of said event from the at least one other region.

3. A display system according to claim 2, wherein the display system is arranged to display an indicium indicative of said elapsed time in said distinguished region.

4. A display system according to claim 1, wherein the display includes a common display region and each selected display mode displays an indicium therein, wherein each of the selectable display modes displays a different indicium in said common display region, each indicium being selectable from a plurality of indicia and representing a different stage of elapsed time in relation to said previous detection of said event.

5. A display system according to claim 1, wherein each of the selectable display modes includes displaying an identifier representative of an integral number of hours corresponding to the stage of elapsed time since the previous detection of said event.

6. A display system according to claim 1, wherein said set of a plurality of different display modes includes a first sub-set of display modes and a second sub-set of display modes, and wherein said invoked plurality of display modes includes a member of said first sub-set and a member of said second sub-set.

7. A display system according to claim 6, wherein the first sub-set of display modes corresponds to the elapsed time between the first and second detections of said event and the second sub-set of display modes corresponds to the elapsed time between the second and third detections of said event.

8. A display system according to claim 1, wherein the invoked display modes in the plurality of invoked display modes are arranged in a sequence on the display and the display system is arranged to sequentially displace each of the invoked display modes in the plurality.

9. A display system according to claim 8, wherein the sequence has a specified length and a first end and a second end, the specified length corresponding to a number of selected display modes, wherein the display system is arranged to sequentially displace each of the selected display modes on the display such that the first end corresponds to a most recent detection of said event and the second end corresponds to a previous detection of said event that is separated from the most recent detection of said event by the specified length.

10. A device including the display system according to claim 1, wherein the usage detected by the detection system relates to usage of the device.

11. A device according to claim 10, wherein the device is a dispenser and the detection system is arranged to detect an event relating to dispensing by the dispenser.

12. A dispenser according to claim 11, wherein the dispenser is a medicament dispenser.

13. A dispenser according to claim 12, where the medicament dispenser comprises an inhalation device adapted either for oral or nasal use.

14. Use of a dispenser according to claim 11 for dispensing a product.

15. A dispensing device for dispensing a product, the device comprising:
   a replaceable refill arranged to store the product;
   an actuator arranged to dispense the product; and
   a display system according to claim 2, wherein the detection system and the display are in operative association with the actuator such that said selected display modes are invoked on the actuator,
   wherein each of the plurality of regions relates to a different time at which said previous detection of said event occurred, each time corresponding to a part of a usage regime for that product, the replaceable refill container being arranged to store data identifying said usage regime and the display system being arranged to retrieve said usage regime data therefrom.

16. A display system for use in displaying data in respect of usage of a device, the display system including:
   a detection system to detect an event that is indicative of usage of the device; and
   a display arranged to display data;
   the display system being arranged to invoke a selected display mode on the display in response to detection of the said event, the display mode being selectable by the display system from a set of a plurality of different display modes in dependence on an elapsed time between detection of the said event and a previous detection of said event, each of the different display modes identifying a different stage of elapsed time between detection of the pair of said events,
   wherein the display system is arranged to invoke a plurality of display modes, each corresponding to a different detection of said event, and the elapsed time upon which the selection of each of the plurality of display modes is based is that between the corresponding detection of said event and a previous detection of said event,
   wherein the invoked display modes in the plurality of invoked display modes are arranged in a sequence on the display and the display system is arranged to sequentially displace each of the invoked display modes in the plurality, and
   wherein the sequence has a specified length and a first end and a second end, the specified length corresponding to a number of selected display modes, wherein the display system is arranged to sequentially displace each of the selected display modes on the display such that the first end corresponds to a most recent detection of said event and the second end corresponds to a previous detection of said event that is separated from the most recent detection of said event by the specified length.

* * * * *